(12) United States Patent
Kennis et al.

(10) Patent No.: US 6,352,999 B1
(45) Date of Patent: Mar. 5, 2002

(54) TRICYLIC DELTA 3-PIPERIDINES AS PHARMACEUTICALS

(75) Inventors: Ludo Edmond Josephine Kennis, Turnhout; Josephus Carolus Mertens, Oud-Turnhout; Mirielle Braeken, Peer, all of (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/806,587

(22) PCT Filed: Oct. 1, 1999

(86) PCT No.: PCT/EP99/07420

§ 371 Date: Mar. 30, 2001

§ 102(e) Date: Mar. 30, 2001

(87) PCT Pub. No.: WO00/20423

PCT Pub. Date: Apr. 13, 2000

(30) Foreign Application Priority Data

Oct. 6, 1998 (EP) .............................. 98203371

(51) Int. Cl.$^7$ ............... A61K 31/4355; A61K 31/4365; C07D 491/48; C07D 495/04; A61P 25/16
(52) U.S. Cl. ..................... 514/291; 546/80; 546/89; 544/333; 514/269
(58) Field of Search ..................... 546/80, 89; 514/291, 514/269; 544/333

(56) References Cited

U.S. PATENT DOCUMENTS 4,740,602 A    4/1988   Bottcher

FOREIGN PATENT DOCUMENTS

| EP | 0 206 225 A | 12/1986 |
| WO | WO 89 45297 A | 10/1998 |

OTHER PUBLICATIONS

International Search Report PCT/EP99/07420.

*Primary Examiner*—Evelyn Mei Huang
(74) *Attorney, Agent, or Firm*—Woodcock Washburn LLP

(57) ABSTRACT

The present invention concerns the compounds of formula

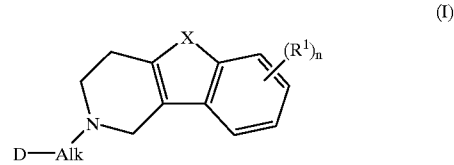

(I)

the N-oxide forms, the pharmaceutically acceptable addition salts and the stereochemically isomeric forms thereof, wherein Alk is $C_{1-6}$alkanediyl; n is 1 or 2; X is —O—, —S—, —S(=O)— or —S(=O)$_2$—; each $R^1$ is independently hydrogen, halogen, $C_{1-6}$alkyl, nitro, hydroxy or $C_{1-4}$alkyloxy; D is an indole, a benzisoxazole, a benzisothiazole, a 2H-benzopyranone, a phenoxyphenyl, a benzamide, a benzophenone or a benzopyrimidinone having central $\alpha_2$-adrenoceptor antagonist activity. It further relates to their preparation, pharmaceutical use and compositions.

10 Claims, No Drawings

TRICYLIC DELTA 3-PIPERIDINES AS PHARMACEUTICALS

CROSS REFERENCE TO RELATED APPLICATIONS

This application is a National Stage application under 35 U.S.C. § 371 of PCT/EP99/07420 filed Oct. 1, 1999, which claims priority from EP 98.203.371.4, filed Oct. 6, 1998.

The present invention concerns tricyclic Δ3-piperidines having central $\alpha_2$-adrenoceptor antagonist activity. It further relates to their preparation, compositions comprising them and their use as a medicine.

Central $\alpha_2$-adrenoceptor antagonists are known to increase noradrenaline release by blocking presynaptic $\alpha_2$-receptors which exert an inhibiting control over the release of the neurotransmitter. By increasing the noradrenaline concentrations, $\alpha_2$-antagonists can be used clinically for the treatment or prophylaxis of depression, cognitive disturbances, Parkinson's disease, diabetes mellitus, sexual dysfunction and impotence, elevated intraocular pressure, and diseases related to disturbed enterokinesia, since all these conditions are associated with a deficiency of noradrenaline in the central or peripheral nervous system.

The compounds of the present invention are novel and have a specific and selective binding affinity for the different known subtypes of the $\alpha_2$-adrenoceptors, i.e. the $\alpha_{2A}$, $\alpha_{2B}$ and $\alpha_{2C}$-adrenoceptor.

The present invention concerns the compounds of formula

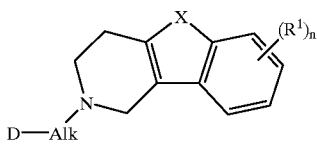
(I)

the N-oxide forms, the pharmaceutically acceptable addition salts and the stereochemically isomeric forms thereof, wherein:

Alk is $C_{1-6}$alkanediyl;
n is 1 or 2;
X is —O—, —S—, —S(=O)— or —S(=O)$_2$—;
each $R^1$ is independently hydrogen, halogen, $C_{1-6}$alkyl, nitro, hydroxy or $C_{1-4}$alkyloxy;
D is a radical of formula

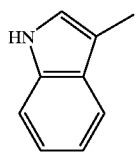
(a)

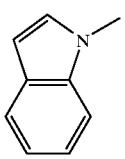
(b)

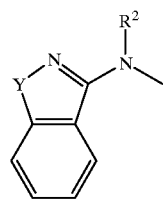
(c)

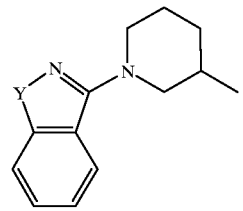
(d)

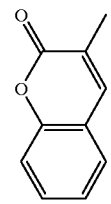
(e)

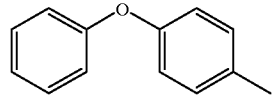
(f)

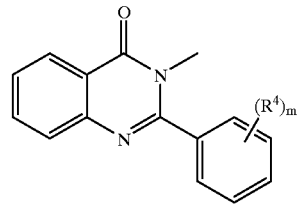
(g)

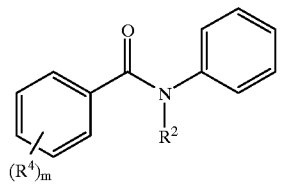
(h)

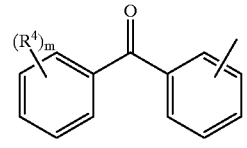
(i)

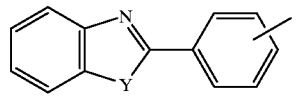
(j)

wherein
each m independently is 0, 1 or 2;
each Y independently represents —CH$_2$—, —O—, —S— or —NR$^3$—;

$R^2$ and $R^3$ each independently are hydrogen or $C_{1-6}$alkyl; and each $R^4$ independently represents halo or $C_{1-6}$alkyl.

As used in the foregoing definitions the term halogen is generic to fluoro, chloro, bromo and iodo. The term $C_{1-4}$alkyl defines straight and branched saturated hydrocarbons, having from 1 to 4 carbon atoms such as, for example, methyl, ethyl, propyl, butyl, 1-methylethyl, 1,1-dimethylethyl, 2-methylpropyl and the like. The term $C_{1-6}$alkyl is meant to include $C_{1-4}$alkyl radicals and the higher homologues thereof having 5 or 6 carbon atoms such as, for example, pentyl, hexyl and the like. The term $C_{1-5}$alkanediyl defines bivalent straight or branch chained alkanediyl radicals having from 1 to 5 carbon atoms such as, for example, methylene, 1,2-ethanediyl, 1,3-propanediyl, 1,4-butanediyl, 1,5-pentanediyl and the like. $C_{1-6}$alkanediyl is meant to include $C_{1-5}$alkanediyl and the higher homologue thereof having 6 carbon atoms such as, for example, 1,6-hexanediyl and the like.

The addition salts as mentioned herein are meant to comprise the therapeutically active addition salt forms which the compounds of formula (I) are able to form with appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, a metal or amine addition salt forms which the compounds of formula (I) are able to form. Said salts can conveniently be obtained by treating the compounds of formula (I) containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted by treatment with an appropriate base or acid into the free acid or base form.

The term addition salt as used hereinabove also comprises the solvates which the compounds of formula (I) are able to form and said solvates are meant to be included within the scope of the present invention. Examples of such solvates are, e.g. the hydrates, alcoholates and the like.

The N-oxide forms of the compounds of formula (I) are meant to comprise those compounds of formula (I) wherein one or several nitrogen atoms are oxidized to the so-called N-oxide.

The term stereochemically isomeric forms as used herein defines all the possible isomeric forms in which the compounds of formula (I) may occur. Unless otherwise mentioned or indicated, the chemical designation of compounds denotes the mixture of all possible stereochemically isomeric forms, said mixtures containing all diastereomers and enantiomers of the basic molecular structure.

Some of the compounds of formula (I) may also exist in their tautomeric forms. Such forms although not explicitly indicated in the above formula are intended to be included within the scope of the present invention.

Whenever used hereinafter, the term compounds of formula (I) is meant to include also the N-oxide forms, the pharmaceutically acceptable addition salts and all stereoisomeric forms.

Suitably, D is a radical of formula (a), (b), (c), (d), (e), (f) or (g) wherein m is 0; each Y independently represents —$CH_2$—, —O—, —S— or —$NR^3$—; and $R^2$ and $R^3$ each independently are hydrogen or $C_{1-6}$alkyl.

As used hereinafter, when the position of the $R^1$ substituent is referred to, the following numbering is used:

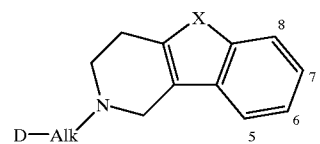

An interesting group of compounds are those compounds of formula (I) wherein n is 1 and $R^1$ is hydrogen, chloro, fluoro, methyl, methoxy or nitro, in particular $R^1$ is hydrogen, chloro, methyl or methoxy. Also interesting are those compounds of formula (I) wherein n is 2 and both $R^1$ are methoxy.

In case $R^1$ is other than hydrogen, then $R^1$ is suitably connected to the tricyclic ring system in the 6 or 7 position.

Another interesting group of compounds are those compounds of formula (I) wherein Alk is methylene, 1,2-ethanediyl, 1,3-propanediyl, 1,4-butanediyl or 1,5-pentanediyl, in particular methylene, 1,2-ethanediyl, 1,3-propanediyl, 1,4-butanediyl, more in particular 1,2-ethanediyl.

Still another interesting group of compounds are those compounds of formula (I) wherein D is a radical of formula (a), (b), (c), (e), (f), (g), (h), (i) or (j), more in particular, (a), (c), (j), (h), (i) or (j).

Compounds of formula (I) wherein D is other than (a) and other than (b) are also of particular interest.

Particular compounds are those compounds of formula (I) wherein X is —O— or —S—, more in particular, —O—.

Other particular compounds are those compounds of formula (I) wherein Y is —O— or —S—.

Preferred compounds are those compounds of formula (I) wherein n is 1, $R^1$ is hydrogen, chloro, methyl or methoxy, and X is —O— or —S—.

Most preferred compounds are those compounds depicted below or their N-oxide forms, the pharmaceutically acceptable addition salts and the stereochemically isomeric forms thereof:

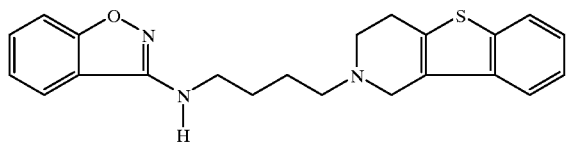

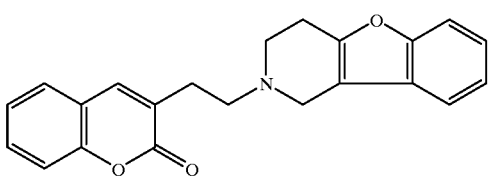

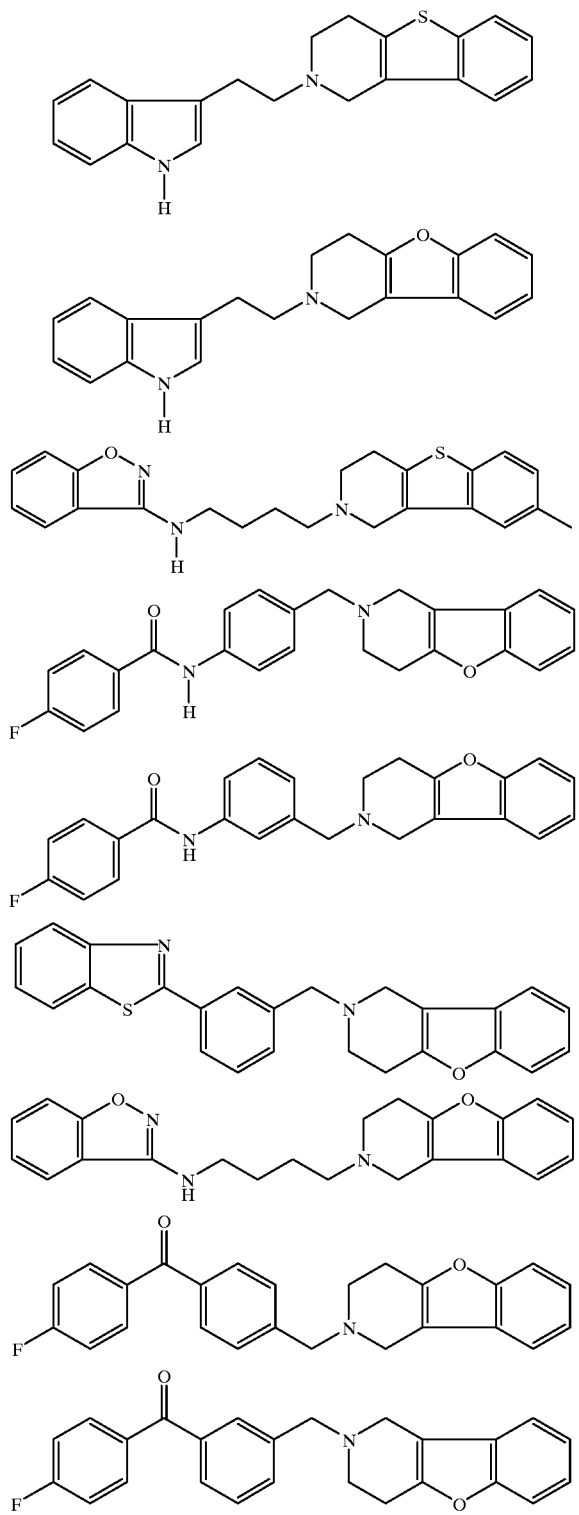

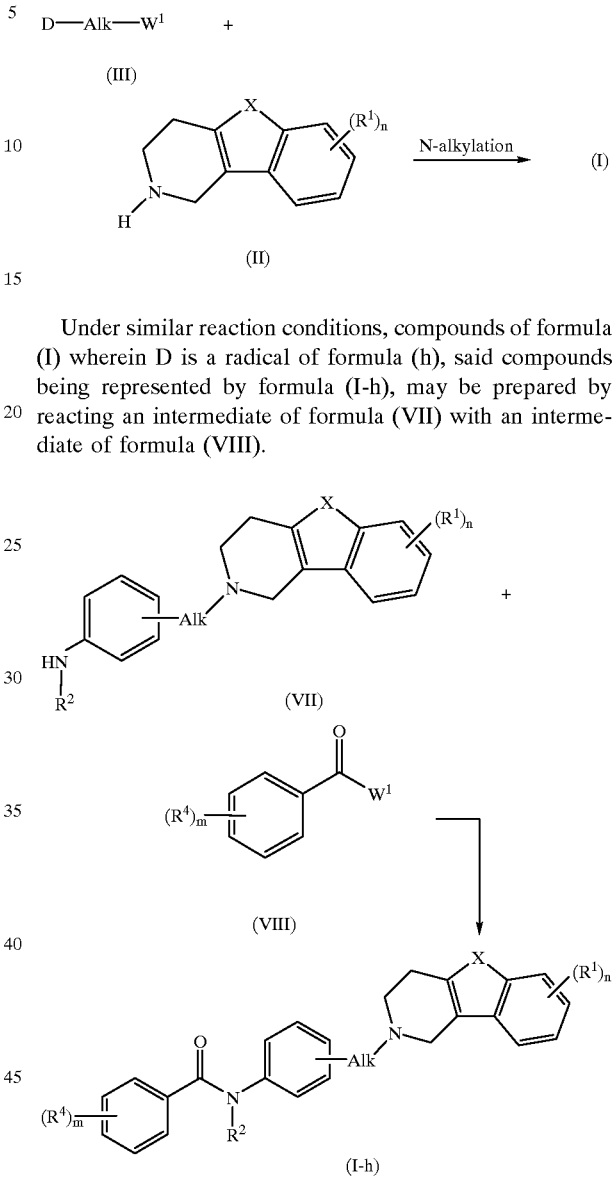

The compounds of formula (I) can generally be prepared by N-alkylating an intermediate of formula (II) with an alkylating reagent of formula (III) following the procedure described in EP-A-0,037,265, EP-A-0,070,053, EP-A-0,196,132 and in EP-A-0,378,255. In particular, the N-alkylation may be performed in a reaction-inert solvent such as, for example, methyl isobutyl keton, N,N-dimethylformamide or N,N-dimethylacetamide, in the presence of a base such as, for example, triethylamine, sodium carbonate or sodiumbicarbonate, and optionally in the presence of a catalyst such as, for example, potassium iodide.

Under similar reaction conditions, compounds of formula (I) wherein D is a radical of formula (h), said compounds being represented by formula (I-h), may be prepared by reacting an intermediate of formula (VII) with an intermediate of formula (VIII).

In intermediate (III) and intermediate (VIII), $W^1$ represents an appropriate reactive leaving group such as, for example, halo, e.g. chloro, bromo or iodo; sulfonyloxy, e.g. methanesulfonyloxy, 4-methylbenzenesulfonyloxy.

In these and the following reactions, the reaction products may be isolated from the reaction medium and, if necessary, further purified according to methodologies generally known in the art such as extraction, crystallization, trituration and chromatography.

A specific way of preparing the compounds of formula (I) wherein D is a radical of formula (c) or (g) and Alk is —(Alk')$_p$—CH$_2$— wherein Alk' is $C_{1-5}$alkanediyl and p is 0 or 1, said compounds being represented by formula (I-g), involves the reductive N-alkylation of an intermediate of formula (II) with an aldehyde derivative of formula (IV-c), respectively (IV-g).

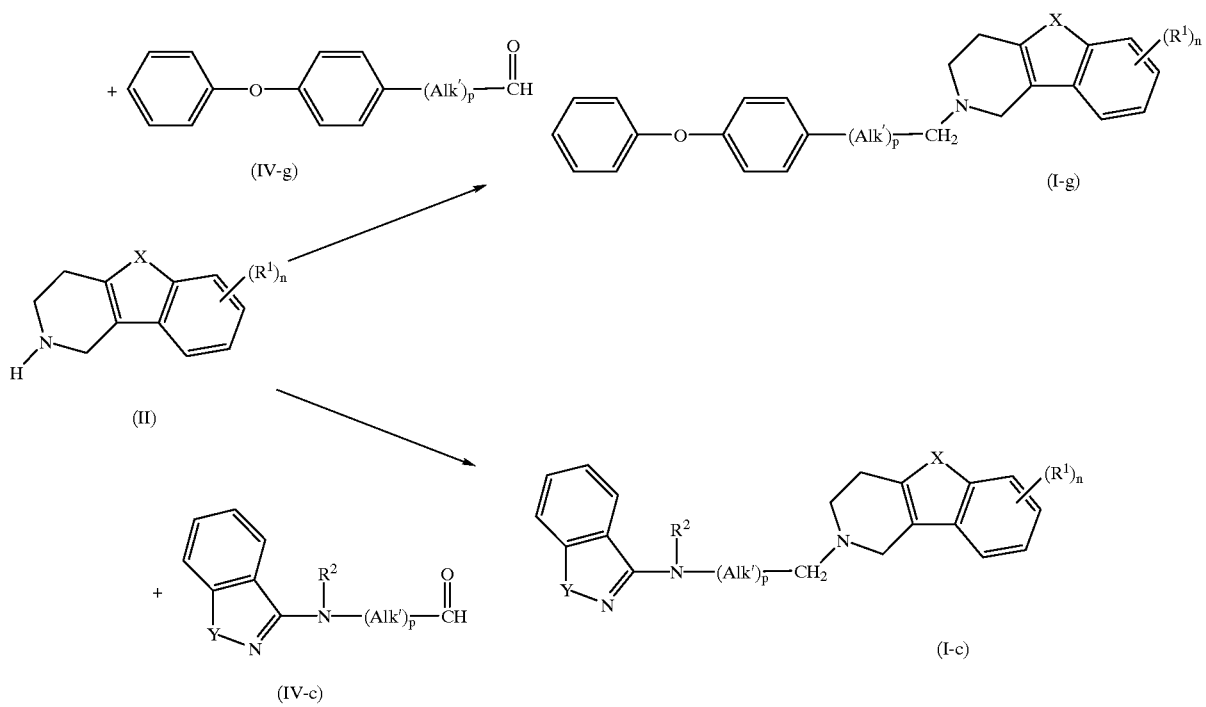

Said reductive N-alkylation reaction may conveniently be carried out by reducing a mixture of the reactants in a suitable reaction-inert solvent following art-known reductive N-alkylation procedures. In particular, the reaction mixture may be stirred and/or heated in order to enhance the reaction rate. Suitable solvents are, for example, water; methanol, ethanol, 2-propanol and the like. The reaction is conveniently carried out either with sodium cyanoborohydride, sodium borohydride, formic acid or a salt thereof and the like reducing agents, or alternatively under hydrogen atmosphere, optionally at an increased temperature and/or pressure, in the presence of an appropriate catalyst such as, for example, palladium-on-charcoal, platinum-on-charcoal and the like. In order to prevent the undesired further hydrogenation of certain functional groups in the reactants and the reaction products, it may be advantageous to add an appropriate catalyst-poison to the reaction mixture, e.g., thiophene, quinoline-sulphur and the like. In some instances it may also be advantageous to add an alkali metal salt to the reaction mixture such as, for example, potassium fluoride, potassium acetate and the like salts.

The compounds of formula (I) may be converted into each other following art-known functional group transformation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A number of intermediates and starting materials are commercially available or are known compounds which may be prepared according to art-known methodologies.

For example, some of the intermediates of formula (III) and their preparations are described in EP-A-0,037,265, EP-A-0,070,053, EP-A-0,196,132 and in EP-A-0,378,255.

Intermediates of formula (II) wherein X is O can be prepared analogous to the procedures described in Cattanach C. et al. (J. Chem. Soc (C), 1971, p53–60); Kartashova T. (Khim. Geterotsikl. Soedin., 1979 (9), p 1178–1180) and Zakusov. V. Et al. (Izobreteniya, 1992 (15), p 247). Intermediates of formula (II) wherein X is S can be prepared analogous to the procedure described in Capps et al. (J. Am. Chem. Soc., 1953, p. 697) or U.S. Pat. No. 3,752,820.

A particular synthesis route for the preparation of intermediates of formula (II) is depicted in scheme 1.

Scheme 1

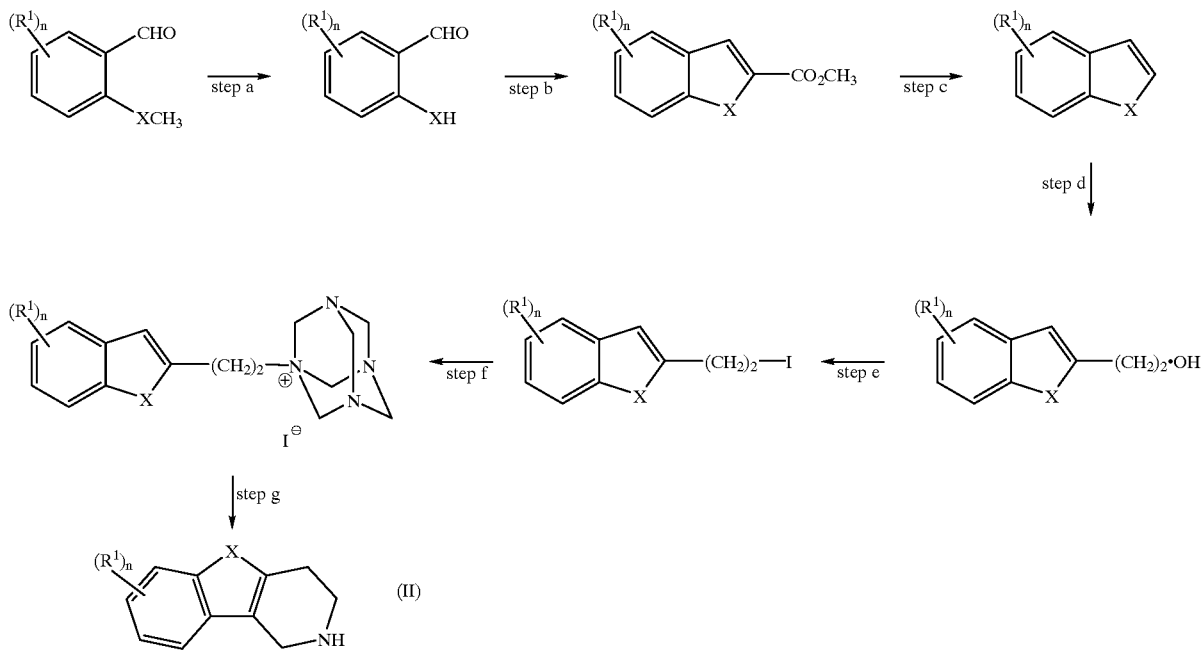

Step a can be performed analogous to the procedure described in Tetrahedron (1981), 37, p 979–982. Benzofurans resulting from step c have been used as intermediates in U.S. Pat. No. 4,210,655. The further reaction steps are analogous to the reaction procedures described in U.S. Pat. No. 3,752,820.

Alternatively, intermediates of formula (II) can be prepared using the reaction steps depicted in scheme 2.

Scheme 2

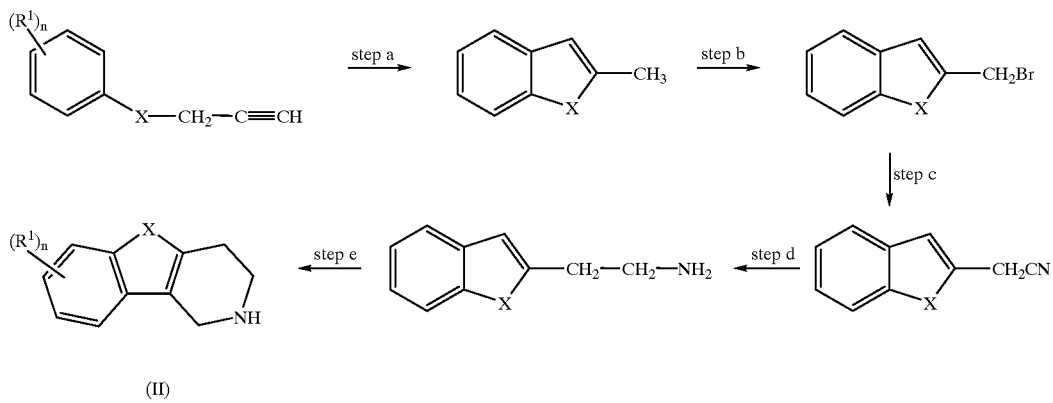

Step a can be performed analogous to the procedure described in Heterocycles (1994), 39(1), p. 371–380. Step b can be performed analogous to the procedure described in J. Med. Chem. (1986), 29(9), p. 1643–1650. Further reaction steps can be performed analogous to the ones described in J. Hetercycl. Chem. (1979), 16, p. 1321.

Intermediates of formula (III) wherein D is a radical of formula (c), said intermediates being represented by formula (III-c), can be prepared by reacting an intermediate of formula (V) wherein $W^2$ is a suitable leaving group such as, for example, a halogen, with an amino-alcohol derivative of formula (VI) in the presence of a catalyst such as, for example, potassium iodide. Conveniently, the reaction mixture is stirred at elevated temperatures. Subsequently, a suitable leaving group such as, for instance, a halogen, e.g. chloro, can be introduced in the thus formed alcohol derivative using art-known techniques such as, for instance, reacting the alcohol with thionylchloride in a solvent such as chloroform.

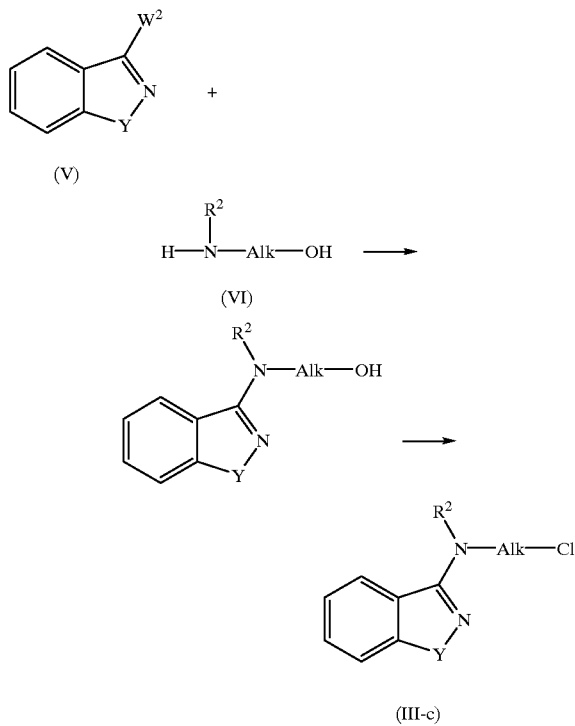

Some of the compounds of formula (I) and some of the intermediates in the present invention contain at least one asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

Pure stereochemically isomeric forms of the compounds of formula (I) may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), the N-oxides, the pharmaceutically acceptable addition salts and stereochemically isomeric forms thereof, block the presynaptic $\alpha_2$-receptors on central noradrenergic neurons thus increasing the noradrenaline release. Blocking said receptors will suppress or relieve a variety of symptoms associated with a deficiency of noradrenaline in the central or peripheral nervous system. Therapeutic indications for using the present compounds are depression, cognitive disturbances, Parkinson's disease, diabetes mellitus, sexual dysfunction and impotence and elevated intraocular pressure.

Blocking $\alpha_2$ receptors in the central nervous system has also been shown to enhance the release of serotonin which may add to the therapeutic action in depression (Maura et al., 1992, Naunyn-Schmiedeberg's Arch. Pharmacol., 345: 410–416).

It has also been shown that blocking $\alpha_2$ receptors may induce an increase of extracellular DOPAC (3,4-dihydrophenylacetic acid) which is a metabolite of dopamine and noradrenaline.

In view of the usefulness of the subject compounds in the treatment of diseases associated with a deficiency of noradrenaline in the central nervous system, in particular depression and Parkinson's disease, the present invention provides a method of treating warm-blooded animals suffering from such diseases, in particular depression and Parkinson's disease, said method comprising the systemic administration of an therapeutically effective amount of a compound of formula (I) or a pharmaceutically acceptable addition salt thereof.

The present compounds are also potentially useful in the treatment of Alzheimer's disease and dementia as it is known that $\alpha_2$-antagonists promote the release of acetylcholine (Tellez et al. 1997, J. Neurochem. 68:778–785).

In general it is contemplated that an effective therapeutic daily amount would be from about 0.01 mg/kg to about 4 mg/kg body weight.

The present invention thus also relates to compounds of formula (I) as defined hereinabove for use as a medicine. Further, the present invention also relates to the use of a compound of formula (I) for the manufacture of a medicament for treating depression or Parkinson's disease.

Ex vivo as well as in vitro receptor signal-transduction and receptor binding studies can be used to evaluate the $\alpha_2$ adrenoceptor antagonism of the present compounds. As indices of central $\alpha_2$-adrenoceptor blockade in vivo, the reversal of the loss of righting reflex observed in rats after intravenous injection of xylazine and inhibition of the tremors induced by reserpine in rats can be used.

The compounds of the present invention also have the ability to rapidly penetrate into the central nervous system.

For administration purposes, the subject compounds may be formulated into various pharmaceutical compositions comprising a pharmaceutically acceptable carrier and, as active ingredient, a therapeutically effective amount of a compound of formula (I). To prepare the pharmaceutical compositions of this invention, an effective amount of the particular compound, in addition salt or in free acid or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Addition salts of (I) due to their increased water solubility over the corresponding free base or free acid form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate the present invention.

EXPERIMENTAL PART

A. Preparation of the Intermediates

Example A1

A mixture of O-phenylhydroxylamine hydrochloride (1:1) (0.625 mol) and 4,4-piperidinediol hydrochloride (1:1) (0.682 mol) in 2-propanol (615 ml) was stirred at 20° C. HCl (353 ml) was added dropwise at 20 ° C. The reaction mixture was gently heated to reflux temperature. The reaction mixture was stirred and refluxed for 3 hours, then cooled to room temperature. The precipitate was filtered off, washed with diisopropyl ether, and dried. This fraction was crystallized from water (1600 ml). The desired compound was allowed to crystallize out while stirring. The precipitate was filtered off, washed with 2-propanol and diisopropyl ether, then dried, yielding 84 g (64%) of 1,2,3,4-tetrahydrobenzo-furo[3,2-c]pyridine hydrochloride (1:1) (interm. 1).

Example A2 a) Butyl lithium (0.27 mol of a 2.5 M solution) was added dropwise to 6-methoxybenzo[b]thiophene [prepared analogous to the procedure described in J. Med. Chem. 1989, 32(12), 2548–2554] (0.25 mol) in tetrahydrofuran (1000 ml), stirred at −30° C. The mixture was stirred for 10 minutes at −30° C. Ethylene oxide (0.38 mol in 100 ml tetrahydrofuran) was added dropwise at −30° C. The mixture was allowed to warm to room temperature and stirred for 3 hours. The mixture was acidified with dilute HCl solution. The solvent was evaporated. The residue was diluted with water and this mixture was extracted with $CH_2Cl_2$. The separated organic layer was dried, filtered and the solvent evaporated. The residue was stirred in hexane, filtered off and dried, yielding 41.3 g of 6-methoxybenzo[b]thiophene-2-ethanol (interm. 2).

b) Methanesulfonylchloride (0.21 mol) was added to a mixture of intermediate (2) (0.19 mol) and triethylamine (0.21 mol) in $CH_2Cl_2$ (1000 ml), stirred at 0° C. The reaction mixture was stirred for 4 hours at room temperature, then poured out into water. The separated organic layer was dried, filtered and the solvent evaporated. The residue was triturated under diisopropylether, filtered off and dried, yielding 50.5 g (94%) of 6-methoxybenzo[b]thiophene-2-ethanol methanesulfonate (ester) (interm. 3).

c) A mixture of intermediate (3) (0.18 mol) and NaI (0.45 mol) in 2-propanone (1000 ml) was stirred and refluxed for 9 hours, then cooled to room temperature and the solvent was evaporated. The residue was washed with water and extracted with $CH_2Cl_2$. The separated organic layer was dried, filtered and the solvent evaporated, yielding 57 g of 2-(2-iodoethyl)-6-methoxybenzo[b]thiophene (interm. 4).

d) Intermediate (4) (0.18 mol) was added portionwise to a mixture of 1,3,5,7-tetra-azatricyclo[5.1.1.13,5]decane (0.45 mol) in $CHCl_3$ (600 ml). The reaction mixture was stirred and refluxed overnight, then cooled to room temperature. The precipitate was filtered off and dried, yielding 54.2 g of 1-[2-(6-methoxybenzo[b]thiophen-2-yl)ethyl]-1,3,5,7-tetraazatricyclo[5.1.1.1 5,7]decanium iodide (interm. 5).

e) A mixture of intermediate (5) (0.12 mol) and HCl (0.50 mol) in ethanol (171 ml) was stirred for 2 days at room temperature. More HCl (10 ml) and ethanol (40 ml) were added and the reaction mixture was stirred and refluxed for one hour, then cooled to room temperature. The solvent was evaporated. The residue was stirred in 2-propanol, then filtered off. The solid was driedand the residue was reconverted into the free base with 20% NaOH. The separated organic layer was dried, filtered and the solvent evaporated. The residue was dissolved in 2-propanol and converted into the hydrochloric acid salt (1:1) with HCl/2-propanol. The precipitate was filtered off and dried, yielding 13.1 g (50%) of 1,2,3,4-tetrahydro-7-methoxy-[1]benzothieno[3,2-c]pyridine (interm. 6).

In an analogous way, there was also prepared:

1,2,3,4-tetrahydro-8-methyl-[1]benzothieno[3,2-c]pyridine hydrochloride (interm. 18).

Example A3 a) A mixture of 3-chloro-1,2-benzisoxazole (0.08 mol), 4-amino-1-butanol (0.24 mol) and potassium iodide (1 g) was stirred for 4 days at 80° C. The reaction mixture was cooled, dissolved in $CH_2Cl_2$ and purified by column chromatography over silica gel (eluent: $CH_2Cl_2/CH_3OH$ 95/5). The pure fractions were collected and the solvent was evaporated, yielding 15.4 g (93%)of 4-(1,2-benzisoxazol-3-ylamino)-1-butanol (interm. 7). b) $SOCl_2$ (0.048 mol) was cooled to 0° C. A solution of intermediate 7 (0.048 mol) in $CHCl_3$ (20 ml) was added dropwise and the reaction mixture was stirred overnight at room temperature. The solvent was evaporated. The residue was washed with water. The reaction mixture was extracted with $CH_2Cl_2$. The separated organic layer was dried, filtered, and the solvent was evaporated, yielding 10.4 g of N-(4-chlorobutyl)-1,2-benzisoxazol-3-amine (interm. 8).

c) Reaction under $N_2$ atmosphere. A solution of ethanedioyl dichloride (0.026 mol) in $CH_2Cl_2$ (60 ml) was stirred at –60° C. Dimethylsulfoxide (3.8 ml) was added dropwise at –60° C. and the mixture was stirred for 10 min. A solution of 4-(1,2-benzisoxazol-3-ylamino)-1-butanol (0.024 mol) in $CH_2Cl_2$ (120 ml) was added dropwise at –60° C. and the mixture was stirred for one hour at –60° C. N,N-diethylethanamine (13.7 ml) was added dropwise and the reaction mixture was stirred for 10 min at –60° C., then allowed to warm to room temperature. The mixture was poured out into water (250 ml). The mixture was stirred for 10 min. The separated organic layer was dried, filtered and the solvent evaporated. The residue was triturated under hexane, filtered off and dried, yielding 3.9 g of 4-(1,2-benzisoxazol-3-ylamino)butanol (80%) (interm.9).

Example A4

To a stirred mixture of 58.5 g of 1H-indole, 107.5 ml of 1-bromo-3-chloropropane, 15 mg of N,N,N-triethylbenzenemethanaminium chloride and 450 ml of benzene were added dropwise, during a period of 30 minutes, 250 ml of a sodium hydride dispersion 60% at 40° C. Upon completion, stirring was continued for 1 hour at 40° C. Another amount of 15 ml of 1-bromo-3-chloropropane was added and stirring was continued for 1 hour at 50° C. After cooling, the reaction mixture was poured into water. The product was extracted with benzene. The extract was separated, dried, filtered and evaporated. The residue was distilled, yielding 80 ml (83%) of 1-(3-chloropropyl)-1H-indole (interm. 10); bp. 120–125° C.

Example A5 a) A mixture of 1,2,3,4-tetrahydrobenzofuro[3,2-c]pyridine hydrochloride (1:1), (0.05 mol), 1-(chloromethyl)-4-nitrobenzene (0.05 mol), $Na_2CO_3$ (7 g) and potassium iodide (0.1 g) in 4-methyl-2-pentanone (250 ml) was stirred and refluxed for 8 hours. The mixture was allowed to cool to room temperature. The reaction mixture was filtered and the filtrate was evaporated. The oily residue was dissolved in $CH_3CN$/diisopropyl ether and stirred. The precipitate was filtered off and dried, yielding 8 g of 1,2,3,4-tetrahydro-2-[(4-nitrophenyl)methyl]benzofuro[3,2-c]pyridine (intern. 11). The filtrate was stirred with HCl/2-propanol. The precipitate was filtered off and dried, yielding 9 g of 1,2,3,4-tetrahydro-2-[(4-nitrophenyl)methyl]benzofuro[3,2-c]pyridine hydrochloride (.HCl) (interm. 12).

b) A mixture of intermediate (11) (0.027 mol) in 2-methoxyethanol (300 ml) was hydrogenated at room temperature with platinum on activated carbon, 5% (2 g) as a catalyst in the presence of thiophene solution (2 ml). After uptake of $H_2$ (3 equiv), the catalyst was filtered off and the filtrate was evaporated. The residue was stirred in diisopropyl ether+a small amount of $CH_3CN$ and treated with HCl/2-propanol. The hydrochloric acid salt (1:2) was filtered off and dried, yielding 8.5 g of 4-[(3,4-dihydrobenzofuro[3,2-c]pyridin-2(1H)-yl)methyl]benzenamine monohydrochloride (interm.13).

Example A6 a) Reaction under $N_2$ atmosphere. $BF_3.Et_2O$ (215 ml) was cooled to 0° C. 3-Fluorophenol (0.25 mol) was added. 6-Chlorohexanoyl chloride (0.51 mol) was added and the resulting reaction mixture was stirred for 15 min at 0° C., then allowed to warm to room temperature. The reaction mixture was then stirred overnight at 130° C. The mixture was cooled to room temperature. Water was added while cooling. This mixture was extracted twice with 2,2'-oxybispropane. The separated organic layer was dried, filtered and the solvent evaporated. The residue was purified by column chromatography over silica gel (eluent: $CH_2Cl_2$/hexane 50/50), then by HPLC (eluent: $CH_2Cl_2$/hexane 50/50). The pure fractions were collected and the solvent was evaporated, 52.2 g of 6-chloro-1-(4-fluoro-2-hydroxyphenyl)-1-hexanone (interm. 14).

b) A mixture of intermediate (14) (0.21 mol) and hydroxylamine (0.25 mol) in pyridine (100 ml) was stirred for 2 days at room temperature, then poured out into 1N HCl (450 ml). This mixture was stirred for 10 min, then extracted with ethylacetate. The separated organic layer was dried, filtered and the solvent evaporated. The residue was purified by column chromatography over silica gel (eluent: $CH_2Cl_2$/$CH_{3OH}$ 99/1). The desired fractions were collected and the solvent was evaporated, yielding 22 g of 6-chloro-1-(4-fluoro-2-hydroxyphenyl)-1-hexanone, oxime (interm. 15).

c) Intermediate (15) (0.077 mol) in tetrahydrofuran (200 ml) was warmed to 60° C. A solution of 1,1'-carbonylbis[1H-imidazole] (0.16 mol) in tetrahydrofuran (600 ml) was added dropwise and the resulting reaction mixture was stirred and refluxed for 2 hours. The reaction mixture was cooled to room temperature and the solvent was evaporated. The residue was washed with water, then acidified with HCl. This mixture was extracted with $CH_2Cl_2$. The separated organic layer was dried, filtered and the solvent evaporated. The residue was purified by column chromatography over silica gel (eluent: $CH_2Cl_2$ 100%). Two desired fraction groups were collected and their solvent was evaporated, yielding 6.4 g of 3-(5-chloropentyl)-6-fluoro-1,2-benzisoxazole (interm. 16) and 11.1 g of 2-(5-chloropentyl)-6-fluorobenzoxazole (interm.17).

Example A7

A mixture of 2-(4-chlorophenyl)-3-(2-hydroxyethyl)-4(3H)-quinazolinone (0.068 mol) and HBr in water 46% (200 ml) was stirred and refluxed for 90 minutes. 300 ml of water was added. The crystallized product was filtered off and dried (fraction 1). The filtrate (oil) was solidified (fraction 2). Both fractions were combined, yielding 23.5 g (78%) of 3-(2-bromoethyl)-2-(4-chlorophenyl)-4(3H)-quinazolinone monohydrobromide; mp. 214.0° C. (interm. 19).

B. Preparation of the Final Compounds

Example B1 a) A mixture of 1,2,3,4-tetrahydrobenzothieno[3,2-c]pyridine [prepared analogous to the procedure described in J. Am. Chem. Soc., 1953, p. 697] (0.012 mol) and 4-phenoxybenzaldehyde (0.012 mol) in methanol (100 ml) was hydrogenated with palladium on activated charcoal (1 g) as a catalyst in the presence of thiophene (1 ml of a 4% solution). After uptake of $H_2$ (1 equiv), the catalyst was filtered off and the filtrate was evaporated. The residue was converted into the (E)-2-butenedioic acid salt (1:1), filtered off and dried, yielding 4.1 g (84%) of 1,2,3,4-tetrahydro-1-[(4-phenoxyphenyl)-methyl] [1]benzothieno[3,2-c]pyridine (E)-2-butenedioate (1:1) (comp. 1).

b) A mixture of intermediate (6) (0.0059 mol) and 4-phenoxybenzaldehyde (0.0076 mol) with potassium acetate (1 g) in methanol (150 ml) was hydrogenated at 50° C. with platinum on activated charcoal (1 g) as a catalyst in the presence of thiophene (1 ml of a 5% solution). After uptake of $H_2$ (1 equiv), the catalyst was filtered off and the solvent was evaporated. The residue was washed with water and extracted with CH$_2$Cl$_2$. The separated organic layer was dried, filtered and the solvent evaporated. The residue was crystallized from 2-propanol, filtered off and dried, yielding 1.2 g (50%) of 1,2,3,4-tetrahydro-7-methoxy-2-[(4-phenoxyphenyl)methyl)][1]-benzothieno[3,2-c]pyridine (comp. 2).

c) A mixture of 8-chloro-1,2,3,4-tetrahydrobenzothieno[3,2-c]pyridine hydrochloride (1:1) (0.01 mol), 4-phenoxybenzaldehyde (0.01 mol) and potassium acetate (1 g) in methanol (150 ml) hydrogenated at 50° C. After uptake of H$_2$ (1 equiv), the catalyst was filtered off and the filtrate was evaporated. The residue was washed with water and this mixture was extracted with CH$_2$Cl$_2$. The separated organic layer was dried, filtered and the solvent evaporated. The residue was converted into the hydrochloric acid salt (1:1), filtered off and dried, yielding 2.9 g of 1,2,3,4-tetrahydro-8-methyl-2-[(4-phenoxyphenyl)methyl]-[1]-benzothieno[3,2,-c)pyridine hydrochloride (69%) (comp. 10).

Example B2 a) Intermediate (10) (0.100 g) was added to a solution of intermediate (1) (0.00048 mol) and Na$_2$CO$_3$ (0.100 g) in N,N-dimethylacetamide (1 ml) and the resulting reaction mixture was stirred overnight at 80° C. The desired compound was isolated and purified by HPLC over Kromasil Spherical underivated silica gel (eluent: CH$_2$Cl$_2$/(CH$_2$Cl$_2$/CH$_3$OH 90/10)/CH$_3$OH (0 minutes) 100/0/0, (10.50 minutes) 0/100/0, (12.50 minutes) 50/0/50, (14.00 minutes) 0/0/100, (15.01–20.00 minutes) 100/0/0). The pure fractions were collected and the solvent was evaporated, yielding 0.045 g 1,2,3,4-tetrahydro-2-[3-(1H-indol-1-yl)propyl] benzofuro[3,2-c]pyridine. (comp. 4).

b) A mixture of 1,2,3,4-tetrahydrobenzothieno[3,2-c]pyridine [prepared analogous to the procedure described in J. Am. Chem. Soc., 1953, p. 697] (0.01 mol), intermediate (8) (0.02 mol) and triethylamine (0.03 mol) in N,N-dimethylacetamide (50 ml) was stirred overnight at 70° C., then cooled to room temperature and the solvent was evaporated. The residue was washed with water and extracted with CH$_2$Cl$_2$. The separated organic layer was dried, filtered and the solvent evaporated. The residue was purified by column chromatography over silica gel (eluent: CH$_2$Cl$_2$/CH$_3$OH 90/10). The desired fractions were collected and the solvent was evaporated. The residue was converted into the (E)-2-butenedioic acid salt (2:1). The precipitate was filtered off and dried, yielding 0.38 g (9%) of N-(1,2-benzisoxazol-3-yl)-1,2,3,4-tetrahydro[1]benzothieno[3,2,-c]pyridine-2-butanamine (E)-2-butenedioate (2:1) (comp. 7).

c) Na$_2$CO$_3$ (0.100 g) was added to a solution of 1,2,3,4-tetrahydro-benzothieno[3,2-c]-pyridine [prepared analogous to the procedure described in J. Am. Chem. Soc., 1953, p. 697] (0.00044 mol) and 3-(2-bromoethyl)-1H-indole (0.100 g) in methyl isobutyl jeton (2 ml) and the resulting reaction mixture was stirred overnight at 100 ° C. The desired compound was isolated and purified by HPLC over Kromasil Spherical underivated silica gel (eluent: CH$_2$Cl$_2$/(CH$_2$Cl$_2$/CH$_3$OH 90/10)/CH$_3$OH (0 minutes) 100/0/0, (10.50 minutes) 0/100/0, (12.50 minutes) 50/0/50, (14.00 minutes) 0/0/100, (15.01–20.00 minutes) 100/0/0). The pure fractions were collected and the solvent was evaporated, yielding 0.045 g of 1,2,3,4-tetrahydro-2-[2-(1H-indol-3-yl)ethyl][1]-benzothieno[3,2-c]pyridine (comp. 8).

d) A mixture of intermediate (1) (0.01 mol), intermediate (17) (0.012 mol), Na$_2$CO$_3$ (3 g) and KI in 4-methyl-2-pentanone (200 ml) was stirred and refluxed overnight and then cooled to room temperature. The solvent was evaporated. The residue was washed with H$_2$O and the mixture was extracted with CH$_2$Cl$_2$. The organic layer was separated, dried, filtered and the solvent was evaporated. The residue was purified by column chromatography over silica gel (eluent: CH$_2$Cl$_2$/CH$_3$OH 90/10). The pure fractions were collected and the solvent was evaporated. The residue was converted into the (E)-2-butenedioic acid salt (1:1). The precipitate was filtered off, and recrystallized from CH$_3$CN/2-propanol. The precipitate was filtered off and dried, yielding 2.0 g of 2-[5-(6-fluoro-2-benzoxazolyl) pentyl]-1,2,3,4-tetrahydrobenzofuro[3,2-c]pyridine (E)-2-butenedioate (1:1) (40%) (comp. 16).

Example B3

Acetic acid (0.0049 mol) was added to intermediate (18) (0.0049 mol) in 1,2-dichloroethane (50 ml). Intermediate (9) (0.0049 mol) was added and the mixture was stirred until complete dissolution. NaHB(OAc)$_3$ (0.0049 mol) was added and the reaction mixture was stirred overnight at room temperature. The reaction mixture was washed with a 10% aqueous NaOH solution (50 ml). The layers were separated. The aqueous phase was re-extracted with CH$_2$Cl$_2$. The separated organic layer was dried, filtered and the solvent evaporated. The residue was purified by column chromatography over silica gel (eluent: CH$_2$Cl$_2$/CH$_3$OH 95/5). The pure fractions were collected and the solvent was evaporated. The residue was converted into the hydrochloric acid salt (1:1) filtered off and dried, yielding 1.3 g of N-(1,2-benzisoxazol-3-yl)-1,2,3,4-tetrahydro-8-methyl-[1]benzothieno[3,2,-c]pyridine-2-butanamine hydrochloride (1:1) (57%) (comp. 11).

Example B4

A mixture of 4-fluorobenzoyl chloride (0.01 mol), intermediate (13) (0.01 mol) and Na$_2$CO$_3$ (4 g) in CHCl$_3$ (100 ml) was stirred and refluxed for 30 min. The mixture was allowed to cool to room temperature. The precipitate was filtered off by suction and the filter cake was stirred in water, then filtered off, stirred in CH$_3$CN, filtered off, washed with diisopropyl ether and dried, yielding 2.4 g of N-[4-[(3,4-dihydrobenzofuro[3,2-c]-pyridin-2(1H)-yl)methyl]phenyl]-4-fluorobenzamide (comp. 14).

Table 1 lists compounds of formula (I) which were prepared according to one of the above examples.

TABLE 1
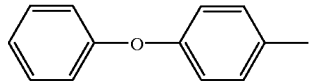
| Co. No. | Ex. No. | R¹ | X | Alk | D | Salt/mp. |
|---|---|---|---|---|---|---|
| 1 | B1a | H | S | CH₂ | 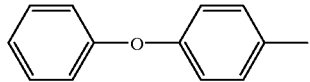 | (E)-2-butenedioate (1:1) |
| 2 | B1b | 8-OCH₃ | S | CH₂ | 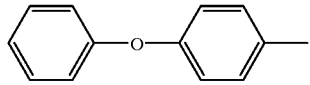 | |
| 3 | B1b | 7-Cl | S | CH₂ | 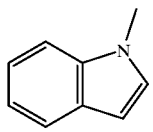 | HCl (1:1) |
| 4 | B2a | H | O | (CH₂)₃ | 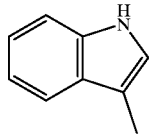 | |
| 5 | B2a | H | O | (CH₂)₂ | 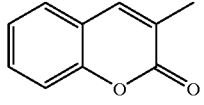 | |
| 6 | B2a | H | O | (CH₂)₂ | 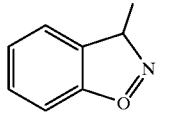 | |
| 7 | B2b | H | S | (CH₂)₄ | 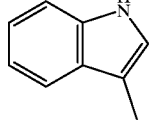 | (E)-2-butenedioate (2:1) |
| 8 | B2c | H | S | (CH₂)₂ | 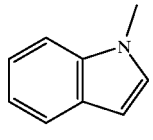 | |
| 9 | B2c | H | S | (CH₂)₃ | 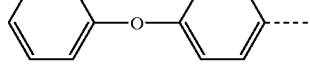 | |
| 10 | B1c | CH₃ | S | CH₂ | | HCl (1:1) |

TABLE 1-continued
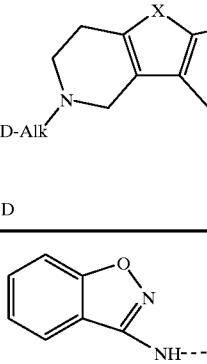
| Co. No. | Ex. No. | R$^1$ | X | Alk | D | Salt/mp. |
|---|---|---|---|---|---|---|
| 11 | B3 | CH$_3$ | S | (CH$_2$)$_4$ | 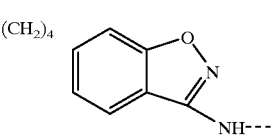 | HCl (1:1) |
| 12 | B3 | 7-OCH$_3$ | S | (CH$_2$)$_4$ | 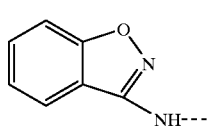 | HCl (1:1) |
| 13 | B3 | 8-Cl | S | (CH$_2$)$_4$ | 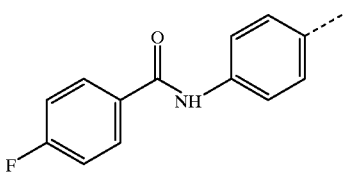 | HCl (1:1) |
| 14 | B4 | H | O | CH$_2$ | 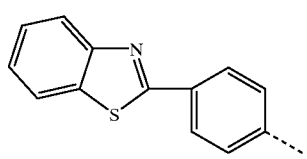 | |
| 15 | B2c | H | O | CH$_2$ | 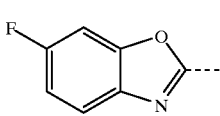 | |
| 16 | B2a | H | O | (CH$_2$)$_5$ | 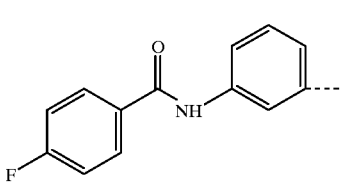 | (E)-2-butenedioate (1:1) |
| 17 | B4 | H | O | CH$_2$ | 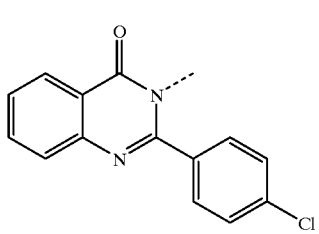 | HCl (1:1) |
| 18 | B2c | H | O | (CH$_2$)$_2$ | | (E)-2-butenedioate (2:1) |

TABLE 1-continued

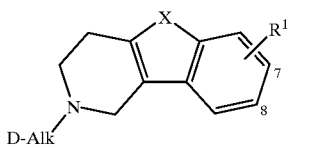

| Co. No. | Ex. No. | R¹ | X | Alk | D | Salt/mp. |
|---|---|---|---|---|---|---|
| 19 | B2c | H | O | $CH_2$ | benzothiazol-2-yl-phenyl | |
| 20 | B3 | H | O | $(CH_2)_4$ | benzisoxazol-3-yl-NH | (E)-2-butenedioate (2:1) |
| 21 | B2c | H | S | $(CH_2)_2$ | 2-(4-chlorophenyl)quinazolin-4(3H)-on-3-yl | (E)-2-butenedioate (1:1) |
| 22 | B2c | H | O | $CH_2$ | 3-(4-fluorobenzoyl)phenyl | HCl (1:1) |
| 23 | B2c | H | O | $CH_2$ | 4-(4-fluorobenzoyl)phenyl | HCl (1:1) |

C. Pharmacological Examples

Example C.1

In Vitro Binding Affinity for $\alpha_2$ Receptors

The interaction of the compounds of formula (I) with $\alpha_2$ receptors was assessed in in vitro radioligand binding experiments.

In general, a low concentration of a radioligand with a high binding affinity for a particular receptor is incubated with a sample of a tissue preparation enriched in a particular receptor or with a preparation of cells expressing cloned human receptors in a buffered medium. During the incubation, the radioligand binds to the receptor. When equilibrium of binding is reached, the receptor bound radioactivity is separated from the non-bound radioactivity, and the receptor bound activity is counted. The interaction of the test compounds with the receptor is assessed in competition binding experiments. Various concentrations of the test compound are added to the incubation mixture containing the receptor preparation and the radioligand. Binding of the radioligand will be inhibited by the test compound in proportion to its binding affinity and its concentration.

The radioligand used for $\alpha_{2A}$, $\alpha_{2B}$ and $\alpha_{2C}$ receptor binding is ³H-rauwolscine and the receptor preparation used is the Chinese Hamster Ovary (CHO) cell expressing cloned human $\alpha_{2A}$, $\alpha_{2B}$ and $\alpha_{2C}$ receptors.

The compounds with number 1 and 5 to 23 to had an $IC_{50}$ value (concentration whereby 50% of the receptors is inhibited) for each of the three receptors of at least $10^{-6}$ M. The other compounds had an $IC_{50}$ value ) for each of the three receptors of at least $10^{-5}$ M.

D. Composition Examples

"Active ingredient" (A.I.) as used throughout these examples relates to a compound of formula (I), a pharmaceutically acceptable addition salt or a stereochemically isomeric form thereof.

Example D.1

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

Example D.2

Film-coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension and the whole is homogenated. The tablet cores are coated with the thus obtained mixture in a coating apparatus.

Example D.3

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example D.4

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

What is claimed is:

1. A compound having the formula

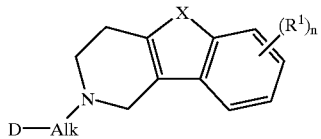

(I)

a N-oxide form, a pharmaceutically acceptable addition salts or a stereochemically isomeric form thereof, wherein:

Alk is $C_{1-6}$alkanediyl;

n is 1 or 2;

X is —O—, —S—, —S(=O)— or —S(=O)$_2$—;

each $R^1$ is independently hydrogen, halogen, $C_{1-6}$alkyl, nitro, hydroxy or $C_{1-4}$alkyloxy;

D is a radical of formula

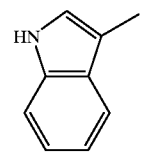

(a)

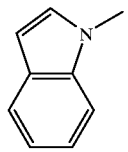

(b)

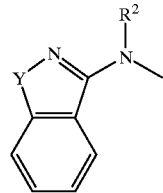

(c)

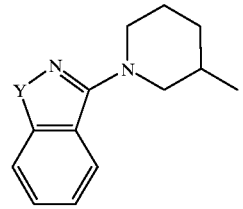

(d)

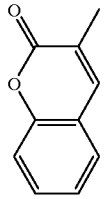

(e)

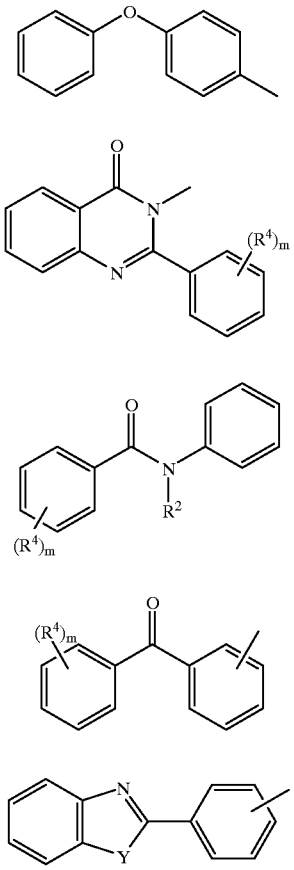

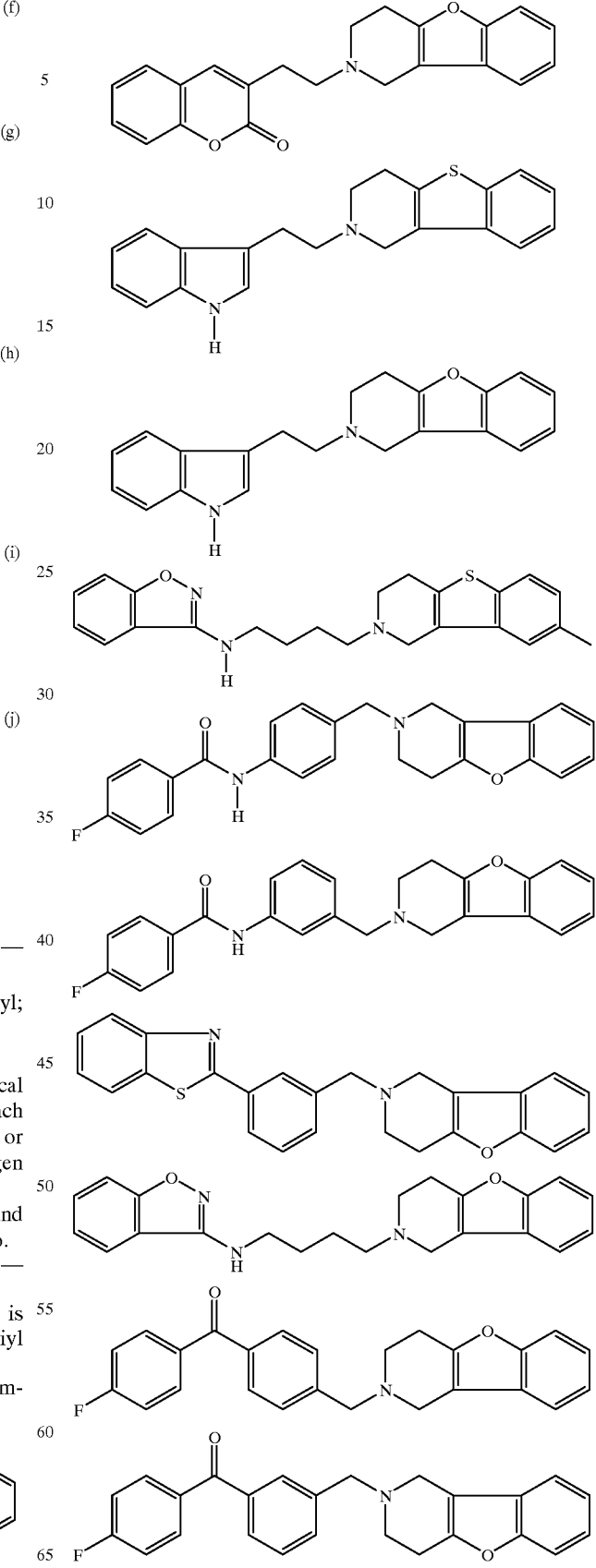

wherein
- each m independently is 0, 1 or 2;
- each Y independently represents —CH$_2$—, —O—, —S— or —NR$^3$—;
- R$^2$ and R$^3$ each independently are hydrogen or C$_{1-6}$alkyl; and
- each R$^4$ independently represents halo or C$_{1-6}$alkyl.

2. A compound according to claim 1 wherein D is a radical of formula (a), (b), (c), (d), (e), (f) or (g) wherein m is 0; each Y independently represents —CH$_2$—, —O—, —S— or —NR$^3$—; and R$^2$ and R$^3$ each independently are hydrogen or C$_{1-6}$alkyl.

3. A compound according to claim 2 wherein n is 1 and R$^1$ is hydrogen, chloro, fluoro, methyl, methoxy or nitro.

4. A compound according to claim 3 wherein X is —O— or —S—.

5. A compound according to claim 4 wherein Alk is methylene, 1,2-ethanediyl, 1,3-propanediyl, 1,4-butanediyl or 1,5-pentanediyl.

6. A compound according to claim 1 wherein the compound is

7. A composition comprising a pharmaceutically acceptable carrier and, as active ingredient, a therapeutically effective amount of a compound as claimed in claim 1.

8. A process for preparing a composition comprising combining a compound of claim 1 as the active ingredient with a pharmaceutically acceptable carrier.

9. A process for preparing a compound according to claim 1, comprising the steps of, a) N-alkylating an intermediate of formula (II) with an alkylating reagent of formula (III)

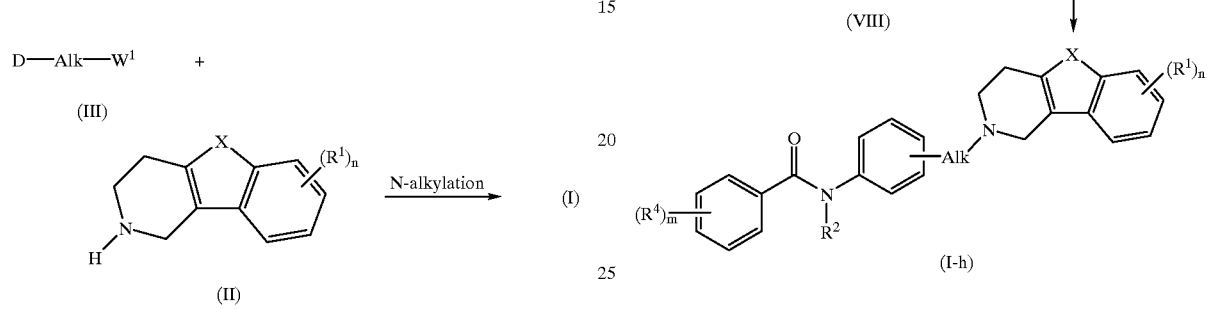

wherein $W^1$ is a suitable leaving group and D, Alk, X, n and $R^1$ are as defined in claim 1, in a reaction-inert solvent, in the presence of a base and optionally in the presence of a catalyst; or b) reacting an intermediate of formula (VII) with an intermediate of formula (VIII)

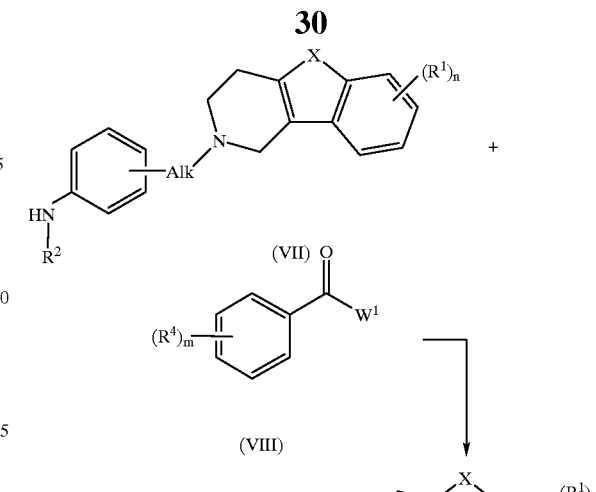

wherein $W^1$ is a suitable leaving group and Alk, X, n, m and $R^1$, $R^2$ and $R^4$ are as defined in claim 1, in a reaction-inert solvent, in the presence of a base and optionally in the presence of a catalyst; thus preparing a compound of formula (I-h); or c) reductive N-alkylating an intermediate of formula (II) with an aldehyde compound of formula (IV-c) or (IV-g)

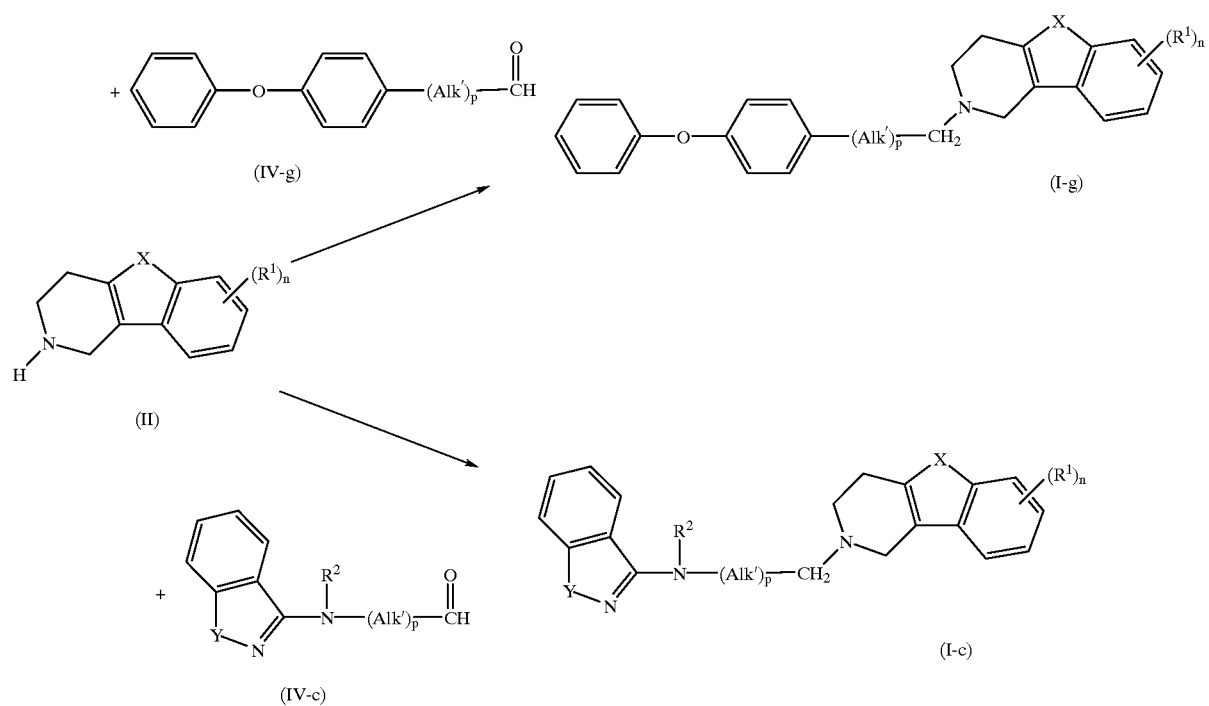

wherein Alk' is $C_{1-5}$alkanediyl, p is 0 or 1 and X, Y, n and $R^1$ are as defined in claim 1, by reducing a mixture of the reactants in a suitable reaction-inert solvent following art-known reductive N-alkylation procedures, thus forming a compound of formula (I-c) or (I-g);

d) and optionally, converting compounds of formula (I) into each other following art-known transformations, and further, optionally, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, optionally, preparing stereochemically isomeric forms or N-oxides thereof.

10. A method for treating a disorder selected from the group consisting of depression and Parkinson's disease in a warm-blooded animal in need thereof comprising administering to the warm-blooded animal a therapeutically effective amount of the compound of claim 1.

\* \* \* \* \*

UNITED STATES PATENT AND TRADEMARK OFFICE
CERTIFICATE OF CORRECTION

PATENT NO.    : 6,352,999 B1
DATED         : March 5, 2002
INVENTOR(S)   : Ludo E. J. Kennis et al.

It is certified that error appears in the above-identified patent and that said Letters Patent is hereby corrected as shown below:

Column 14,
Line 39, "driedand" should be -- dried and --

Column 16,
Line 16, "$CH_{30H}$" should be -- $CH_3OH$ --

Signed and Sealed this

Eleventh Day of June, 2002

Attest:

JAMES E. ROGAN
Attesting Officer    Director of the United States Patent and Trademark Office